US00PP36710P2

(12) United States Plant Patent
Grazzini

(10) Patent No.: US PP36,710 P2
(45) Date of Patent: May 27, 2025

(54) ***DIANTHUS* PLANT NAMED 'G19159'**

(50) Latin Name: *Dianthus hybrida*
Varietal Denomination: G19159

(71) Applicant: Garden Genetics llc, Columbus, OH (US)

(72) Inventor: Richard A. Grazzini, Columbus, OH (US)

(73) Assignee: Garden Genetics, Columbus, OH (US)

( * ) Notice: Subject to any disclaimer, the term of this patent is extended or adjusted under 35 U.S.C. 154(b) by 0 days.

(21) Appl. No.: 18/925,753

(22) Filed: Oct. 24, 2024

(51) Int. Cl.
*A01H 5/02* (2018.01)
*A01H 6/30* (2018.01)

(52) U.S. Cl.
USPC ..... Plt./273

(58) Field of Classification Search
USPC ..... Plt./263.1, 272, 273
See application file for complete search history.

(56) References Cited

U.S. PATENT DOCUMENTS

PP14,549 P3 * 2/2004 Whetman ..... A01H 5/02 Plt./282
PP29,222 P2 * 4/2018 Hansen ..... A01H 6/305 Plt./272

* cited by examiner

*Primary Examiner* — Karen M Redden
(74) *Attorney, Agent, or Firm* — Cassandra Bright

(57) ABSTRACT

A new and distinct cultivar of *Dianthus* plant named 'G19159' is disclosed, characterized by large bright magenta flowers with rounded, overlapping petals. Healthy mid-green foliage exhibits good field tolerance to common *Dianthus* pathogens. The new variety is a *Dianthus*, normally used for outdoor ornamental purposes.

2 Drawing Sheets

Figure 1:
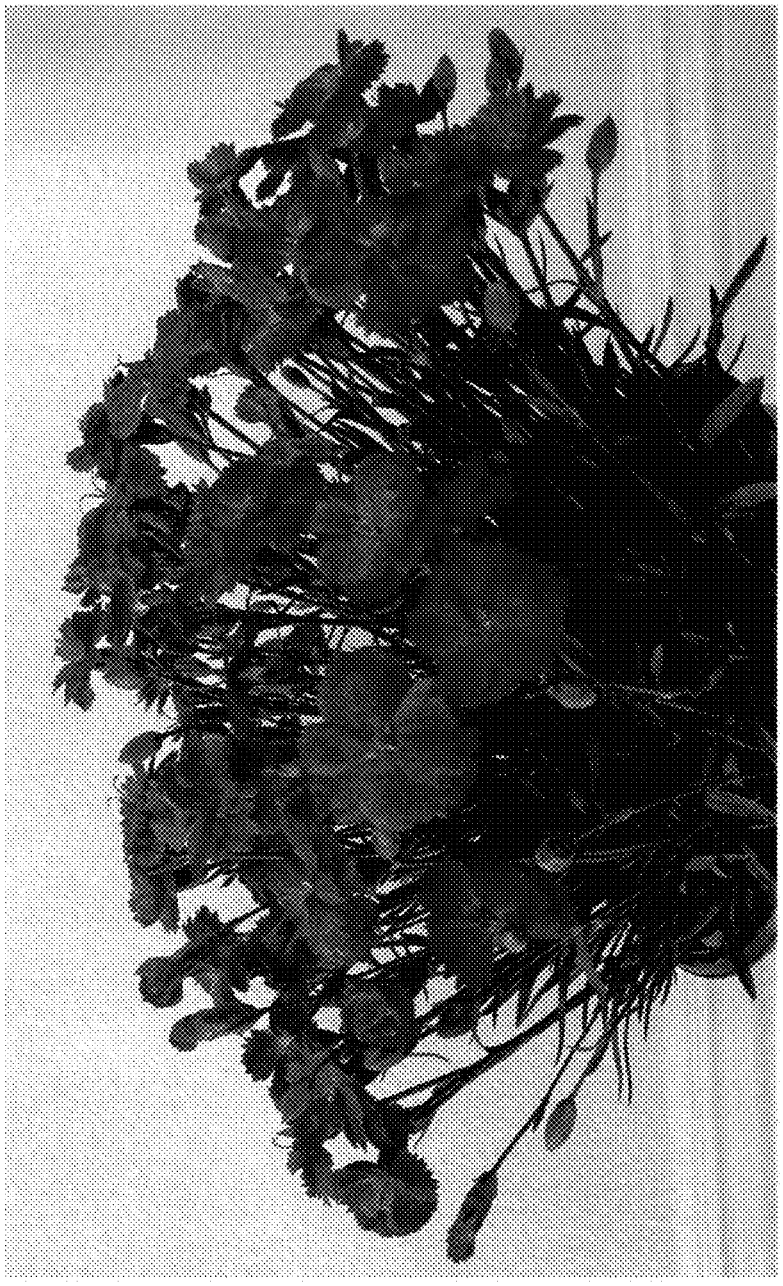

Latin name of the genus and species: *Dianthus hybrida.*
Variety denomination: 'G19159'.

BACKGROUND OF THE INVENTION

The new *Dianthus* cultivar is a product of a planned breeding program conducted by the inventor at a research nursery in Bellefonte, Pennsylvania. The cross resulting in this new variety was made in November of 2018.

The seed parent is the unpatented proprietary variety referred to as *Dianthus* '50527-1'. The pollen parent is the unpatented proprietary variety referred to as *Dianthus* '50263-3'. The new variety was selected in June of 2019 by the inventor in a group of seedlings resulting from the 2018 cross-pollination, in a nursery in Bellefonte, Pennsylvania.

Asexual reproduction of the new cultivar was performed by vegetative cuttings. This was first performed at the same nursery in Bellefonte, Pennsylvania during July of 2019, and has shown that the unique features of this cultivar are stable and reproduced true to type in multiple successive generations.

SUMMARY OF THE INVENTION

The cultivar 'G19159' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'G19159'. These characteristics in combination distinguish 'G19159' as a new and distinct *Dianthus* cultivar:

1. Large flowers.
2. Bright magenta flowers with rounded, overlapping petals.
3. Spreading and dense ground-cover habit.
4. Healthy mid-green foliage.
5. Field tolerance to common *Dianthus* pathogens.
6. Strongly reblooming to constant flowering.

PARENT COMPARISONS

Plants of the new cultivar 'G19159' are similar to plants of the seed parent in most horticultural characteristics; however, plants of the new cultivar 'G19159' differ in the following:

1. Flowers of the new variety are larger than flowers of the seed parent.
2. Flower color of the new variety is bright magenta, while the flower color of the seed parent is pink to red.
3. Flowers of the new variety have no eye, while flowers of the seed parent have a slight eye.
4. Foliage of the new variety is mid-green, while foliage of the seed parent is slightly glaucous.

Plants of the new cultivar 'G19159' are similar to plants of the pollen parent in most horticultural characteristics; however, plants of the new cultivar 'G19159' differ in the following:

1. Flowers of the new variety are larger than flowers of the pollen parent.
2. Flower color of the new variety is bright magenta, while the flower color of the pollen parent is rose-pink.
3. Flowers of the new variety have no eye, while flowers of the pollen parent have a slight eye.
4. Foliage of the new variety is mid-green, while foliage of the pollen parent is silver-grey.

5. Plants of the new variety do not die back in the center, while plants of the pollen parent show slight dieback.

COMMERCIAL COMPARISONS

Plants of the new cultivar 'G19159' are comparable to the commercial variety *Dianthus* 'Kahori', unpatented. The two *Dianthus* varieties are similar in most horticultural characteristics, however, the new variety 'G19159' differs in the following:

1. Flowers of the new variety are larger than flowers of this comparator.
2. Bloom time of the new variety is extended compared to the bloom time of this comparator.
3. The new variety has healthy leaves and plant crown, while this comparator tends to develop an open crown due to plant pathogens. This comparator is also prone to developing leaf spots caused by foliar pathogens.
4. Plants of the new variety are slightly taller than plants of this comparator.
5. Plants of the new variety are somewhat wider than plants of this comparator.

Plants of the new cultivar 'G19159' are comparable to the commercial variety *Dianthus* 'Uribest52', U.S. Plant Pat. No. 28,239. The two *Dianthus* varieties are similar in most horticultural characteristics; however, the new variety 'G19159' differs in the following:

1. Flowers of the new variety are larger than flowers of this comparator.
2. Bloom time of the new variety is extended compared to the bloom time of this comparator.
3. Plants of the new variety are slightly taller than plants of this comparator.
4. Plants of the new variety are wider than plants of this comparator.
5. Foliage of the new variety is mid-green, while foliage of this comparator is dark green.

BRIEF DESCRIPTION OF THE PHOTOGRAPHS

The accompanying photograph in FIG. 1 illustrates a typical flowering plant of 'G19159' grown outdoors in Camarillo, CA at approximately 5-months old in a 1-gallon pot.

Figure 2:
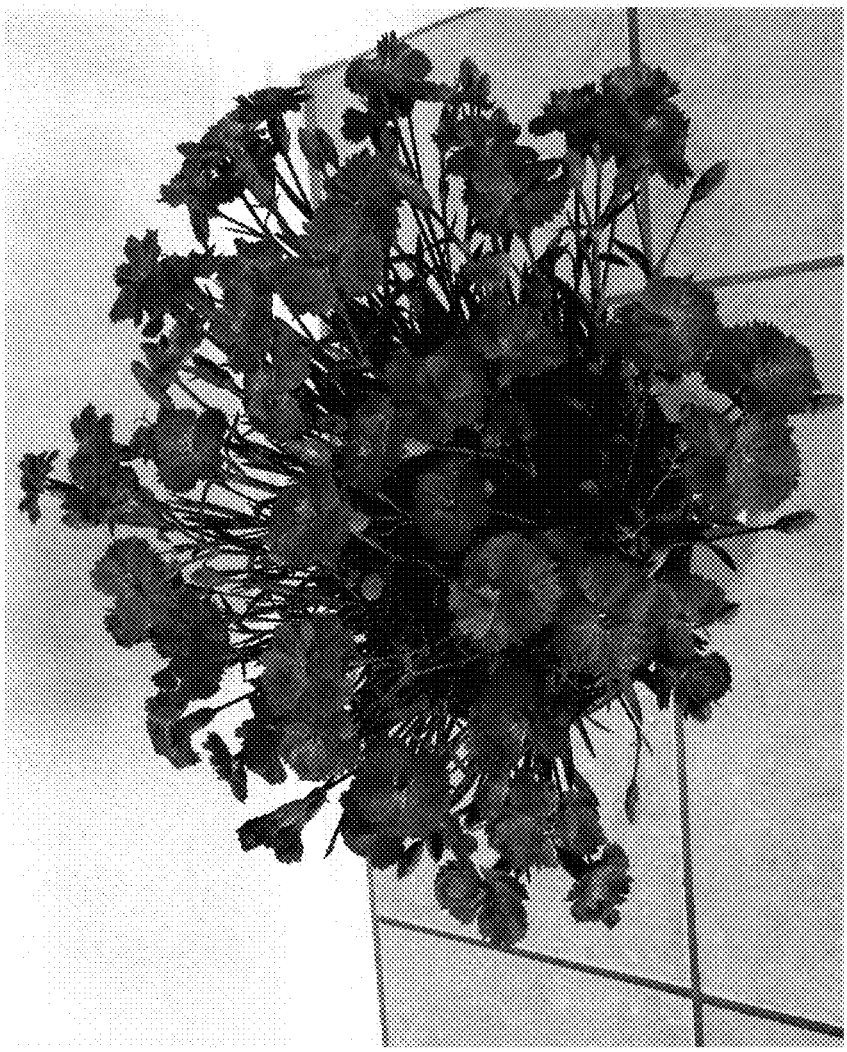

FIG. 2 illustrates a top view of the same plant.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'G19159' plants grown outdoors in Camarillo, California. The growing temperature ranged from approximately 10° C. to 25° C. during the day and from approximately 6° C. to 12° C. during the night. General light conditions are normal sunlight and numerical values represent averages of typical plant types. Measurements were taken during June of 2021.

Botanical classification: *Dianthus hybrida* 'G19159'.

PROPAGATION

Time to initiate roots: About 10 days at approximately 24° C.

Time to produce a rooted cutting: About 18 days at 24° C.

Root description: Fibrous roots, approximately 1 to 3 mm in diameter, colored near RHS Orange-White 159C.

PLANT

Age of plant described: About 22 weeks from a rooted cutting.

Container size of plant described: 4 liters.

Growth habit: Mounded flowering perennial.

Plant spread: About 32 cm.

Plant height: About 24 cm.

Plant vigor: Strong.

Length of plant stem: Average 10 to 16 cm.

Diameter of plant stem: Approximately 3 mm.

Quantity stems: Approximately 50 to 70.

Stem:

*Color*.—Near RHS Greyed-Green 189B.

*Texture*.—Smooth.

*Hollowness*.—Not observed on a plant of this age.

Internode length: 3 to 6 cm.

FOLIAGE

Leaf:

*Arrangement*.—Opposite (in pairs). Quantity: Approximately 4 to 8 per stem.

*Average length*.—4.5 to 5.5 cm.

*Average width*.—4 to 5 mm.

*Shape of blade*.—Linear.

*Apex*.—Acute.

*Base*.—Clasping.

*Attachment*.—Sessile.

*Margin*.—Entire.

*Texture of top surface*.—Smooth.

*Texture of bottom surface*.—Smooth.

*Pubescence*.—None.

*Color*.—Young foliage upper side: Near RHS Greyed-Green 189A. Young foliage under side: Near RHS Greyed-Green 189A. Mature foliage upper side: Near RHS Green 137A with glaucous layer of 189B. Mature foliage under side: Near RHS Green 137A with glaucous layer of 189B.

*Venation*.—Type: Linear. Venation color upper side: Indistinguishable from foliage. Venation color under side: Indistinguishable from foliage.

FLOWER

Natural flowering season: Late spring into fall.

Inflorescence type and habit: Umbel of 2 to 4 flowers, 1 to 2 flowers per stem.

Flower longevity on plant: About 14 days.

Quantity of flowers: Approximately 70 to 80 flowers and buds on a 22-week-old plant.

Persistence: Persistent.

Fragrance: Faint sweet scent.

Inflorescence (umbel) size:

*Diameter*.—Approximately 5 to 7 cm.

*Height*.—Approximately 3 to 5 cm.

Individual flower size:
*Diameter*.—Approximately 4 cm.
*Length*.—Approximately 3 cm.
Petals:
*Arrangement*.—Single overlapping whorl.
*Shape*.—Spatulate, elongated base.
*Base*.—Long attenuate.
*Margin*.—Serrated.
*Apex*.—Serrate.
*Length*.—Upper section, outside of tube: 1.8 cm. Elongated base, in tube: 1.8 cm.
*Width*.—Upper section, outside of tube: 1.8 cm. Elongated base, in tube: 4 mm.
*Petal quantity*.—Average 10 to 12.
*Texture*.—Smooth all surfaces.
*Aspect*.—Nearly flat.
*Color*.—When opening: Upper surface: Near RHS Red-Purple N74C, flushed Red-Purple 71A. Lower surface: Near RHS Red-Purple N74D, flushed Red-Purple 72C. Fully opened: Upper surface: Near RHS Red-Purple 71A, streaked Red-Purple 67D. Lower surface: Near RHS Red-Purple N74D flushed Red-Purple 72C.
Tube:
*General description*.—Tube consists of the elongated, unfused base of the petals. Tube shape caused by a fused calyx.
*Length*.—1.7 cm.
*Width*.—9 mm.
*Texture*.—Smooth.
*Color*.—Fully opened: Inner surface: Near RHS Green 138B. Outer surface: Near RHS Green 138A.
Bud:
*Shape*.—Elongated cylinder.
*Length*.—Average 1.8 cm.
*Diameter*.—Average 9 mm.
*Color*.—Appearing petals colored near RHS Red-Purple 72B.
Sepals:
*Quantity*.—5.
*Arrangement*.—Fused tube.
*Shape*.—Cylindric.
*Length*.—1.5 cm.
*Width*.—5 mm.
*Margin*.—Entire.
*Apex*.—Acute.
*Texture*.—Smooth, upper and lower surfaces.
*Color*.—Near RHS Green 138B.
Bracteoles:
*Shape*.—Deltoid.
*Quantity*.—2-5 per flower.
*Length*.—Average 6 mm.
*Width*.—Average 4 mm.
*Margin*.—Entire.
*Texture*.—Smooth.
*Color*.—Near RHS Green 138B.
Peduncle:
*Length*.—Average 4.5 cm.
*Diameter*.—3 mm.
*Color*.—Near RHS Green 138A, with glaucous layer of Green 189B.
*Orientation*.—Upright.
*Strength*.—Moderate.
*Texture*.—Smooth.

REPRODUCTIVE ORGANS

Stamens:
*Number*.—About 8 to 10.
*Filament length*.—1.8 cm.
*Filament color*.—Near RHS White 155C.
Anthers:
*Shape*.—Linear.
*Length*.—3 mm.
*Color*.—RHS Violet 84C.
*Pollen*.—Not observed.
Pistil:
*Number*.—1, 2 stigmas.
*Length*.—3.5 cm.
*Style*.—Number: 2. Length: Approximately 2.8 cm. Color: Base near RHS White 155C, upper-section Purple 75B.
*Stigma*.—Shape: Linear. Color: Near RHS Purple 77B.
*Ovary*.—Shape: Oblong. Diameter: 7 mm. Length: 9 mm. Color: Near RHS Yellow-Green 145D.

OTHER CHARACTERISTICS

Fruits and seeds: Not observed to date.
Disease/pest resistance: Shows good field-tolerance to common *Dianthus* pathogens. Specific pathogens resistance has not been determined.
Temperature range: Winter hardiness to at least USDA Zone 5.

What is claimed is:

1. A new and distinct cultivar of *Dianthus* plant named 'G19159' as herein illustrated and described.

* * * * *